(12) United States Patent
Bulusu et al.

(10) Patent No.: US 7,759,357 B2
(45) Date of Patent: Jul. 20, 2010

(54) PHENYLPYRIMIDINE AMINES AS IGE INHIBITORS

(75) Inventors: Murty Bulusu, Perchtoldsdorf (AT); Peter Ettmayer, Vienna (AT); Klaus Weigand, Vienna (AT); Max Woisetschlager, Perchtoldsdorf (AT)

(73) Assignee: Novartis AG, Basel (CH)

( * ) Notice: Subject to any disclaimer, the term of this patent is extended or adjusted under 35 U.S.C. 154(b) by 583 days.

(21) Appl. No.: 11/805,515

(22) Filed: May 23, 2007

(65) Prior Publication Data

US 2007/0281956 A1    Dec. 6, 2007

Related U.S. Application Data

(63) Continuation of application No. 10/501,445, filed as application No. PCT/EP03/00973 on Jan. 31, 2003, now abandoned.

(30) Foreign Application Priority Data

Feb. 1, 2002   (GB) ................ 0202381.0
Sep. 20, 2002  (GB) ................ 0221953.3

(51) Int. Cl.
    *C07D 239/42*  (2006.01)
    *A61K 31/505*  (2006.01)
(52) U.S. Cl. ............... 514/275; 544/330; 544/332
(58) Field of Classification Search ........... 544/330, 544/332; 514/275
    See application file for complete search history.

(56) References Cited

U.S. PATENT DOCUMENTS

| | | | |
|---|---|---|---|
| 4,351,939 A | 9/1982 | Simms et al. | 544/230 |
| 4,602,015 A | 7/1986 | Crisafulli et al. | 514/252 |
| 4,659,363 A | 4/1987 | Hubele et al. | 71/92 |
| 4,694,009 A | 9/1987 | Hubele et al. | 514/269 |
| 4,802,909 A | 2/1989 | Rempfler et al. | 71/92 |
| 4,808,333 A | 2/1989 | Huynh-ba et al. | 252/299.66 |
| 4,973,690 A | 11/1990 | Rempfler et al. | 544/279 |
| 4,999,046 A | 3/1991 | Rempfler | 71/92 |
| 5,017,466 A | 5/1991 | Kobayashi et al. | 430/558 |
| 5,159,078 A | 10/1992 | Rempfler et al. | 544/330 |
| 5,516,775 A | 5/1996 | Zimmermann et al. | 514/224.2 |
| 5,521,184 A | 5/1996 | Zimmermann | 514/252 |
| 6,107,301 A | 8/2000 | Aldrich et al. | 514/258 |
| 6,187,781 B1 | 2/2001 | Nakazato et al. | 514/275 |
| 6,576,631 B1 | 6/2003 | Shibata et al. | 514/241 |

FOREIGN PATENT DOCUMENTS

| | | |
|---|---|---|
| EP | 0 013 143 | 7/1980 |
| EP | 0 109 340 | 5/1984 |
| EP | 0 164 204 | 12/1985 |
| EP | 0 233 461 | 8/1987 |
| EP | 0 243 136 | 10/1987 |
| EP | 0 254 259 | 1/1988 |
| EP | 0 310 370 | 4/1989 |
| EP | 1 052 238 | 11/2000 |
| EP | 1 180 520 | 2/2002 |
| GB | 1185039 | 3/1970 |
| GB | 2 001 069 | 1/1979 |
| WO | 95/09847 | 4/1995 |
| WO | 95/09851 | 4/1995 |
| WO | 95/09853 | 4/1995 |
| WO | 96/05177 | 2/1996 |
| WO | 97/19065 | 5/1997 |
| WO | 98/24782 | 6/1998 |
| WO | 98/43968 | 10/1998 |
| WO | 99/19305 | 4/1999 |
| WO | 99/35140 | 7/1999 |
| WO | 99/50250 | 10/1999 |
| WO | 00/18758 | 4/2000 |
| WO | 00/39101 | 7/2000 |
| WO | 00/78731 | 12/2000 |
| WO | 01/58881 | 8/2001 |

OTHER PUBLICATIONS

Robinson, Medical Therapy of Inflammatory Bowel Disease for the 21st century, Eur. J. Surg. 164, Suppl. 582, pp. 90-98, (1998).

*Primary Examiner*—Deepak Rao
(74) *Attorney, Agent, or Firm*—Sophie Binet Cross

(57) ABSTRACT

An amine, which is substituted by phenyl-substituted pyrimidin; and phenyl; and a third substituent and its use as an immunoglobulin E (IgE) inhibitor.

7 Claims, No Drawings

PHENYLPYRIMIDINE AMINES AS IGE INHIBITORS

This is a continuation of application Ser. No. 10/501,445 filed on Jul. 13, 2004, which is National Stage of International Application No. PCT/EP03/00973 filed on Jan. 31, 2003, the entire disclosures of which are hereby incorporated by reference.

The present invention relates to organic compounds, e.g. substituted amines having pharmaceutical e.g. IgE-synthesis inhibiting, activity.

In one aspect the present invention provides a compound of formula

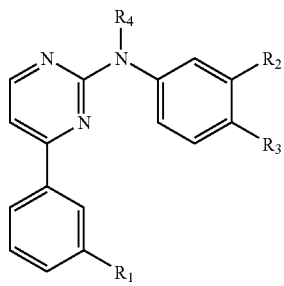

I wherein
$R_1$ is halogen or halo($C_{1-4}$)alkyl,
$R_2$ is hydrogen, halogen or halo($C_{1-4}$)alkyl,
$R_3$ is halogen or halo($C_{1-4}$)alkyl,
$R_4$ is hydrogen, ($C_{1-8}$)alkyl, hydroxy($C_{1-6}$)alkyl or a group of formula
—CO—$R_5$,
—CO—$(CH_2)_m$—$OR_6$,
—CO—CO—$R_7$,
—CO—CO—$OR_8$,
—CO—N($R_9R_{10}$),
—CO—$(CH_2)_n$—CO—$R_{11}$,
—CO—$(CHR_{15})$—O—$(CH_2)_o$—CO—$R_{11}$,
—CO—$(CH_2)_p$—O—$(CH_2)_q$—O—$(CH_2)_r$—$R_{16}$,
—CO—O—$(CH_2)_s$—O—CO—$R_{17}$,
—CO—O—$(CH_2)_t$—N($R_{18}R_{19}$),
—CO—O—$(CH_2)_u$—NH—CO—CH($NH_2$)—$R_{20}$, or
—CO—O—$(CH_2)_w$—NH—CO—$R_{17}$, wherein
$R_5$ is hydrogen, ($C_{1-8}$)alkyl, ($C_{3-8}$)cycloalkyl, amino, ($C_{1-4}$)alkylamino, di($C_{1-4}$)alkylamino, aryl or heterocyclyl which is a 5 or 6-membered heterocyclic ring system having 1 to 4 heteroatoms selected from N, O or S,
$R_6$ is hydrogen, ($C_{1-4}$)alkyl, ($C_{3-8}$)cycloalkyl, aryl, ($C_{1-4}$)alkyl substituted by heterocyclyl which is a 5 or 6-membered heterocyclic ring system having 1 to 4 heteroatoms selected from N, O or S, amino($C_{1-6}$) alkyl, ($C_{1-4}$)alkylamino($C_{1-6}$)alkyl, di($C_{1-4}$)alkylamino($C_{1-6}$)alkyl, hydroxy($C_{1-6}$)alkyl, hydroxy($C_{1-4}$)alkylamino($C_{1-6}$)alkyl or an amino acid residue, e.g. —$CH_2$—CH($NH_2$)—COOH,
$R_7$ and $R_8$ independently of each other are ($C_{1-4}$)alkyl, ($C_{3-8}$)cycloalkyl, aryl or heterocyclyl which is a 5 or 6-membered heterocyclic ring system having 1 to 4 heteroatoms selected from N, O or S,
$R_9$ and $R_{10}$ independently of each other are hydrogen or ($C_{1-4}$)alkyl or one of $R_9$ and $R_{10}$ is hydrogen and the other is ($C_{3-8}$)cycloalkyl, ($C_{1-4}$)alkyl, aryl or heterocyclyl,
$R_{11}$ is ($C_{1-4}$)alkyl, —$OR_{12}$, —$NR_{13}R_{14}$, an amino acid, an ($C_{1-4}$)alkylester thereof or a di($C_{1-4}$)alkylester thereof,
$R_{12}$ is hydrogen or ($C_{1-4}$)alkyl,
$R_{13}$ and $R_{14}$ independently of each other are hydrogen, ($C_{1-4}$)alkyl, amino($C_{1-6}$)alkyl, ($C_{1-4}$)alkylamino($C_{1-6}$)alkyl, di($C_{1-4}$)alkylamino($C_{1-6}$)alkyl,
$R_{15}$ is hydrogen or ($C_{1-4}$)alkyl,
$R_{16}$ is hydrogen, ($C_{1-4}$)alkyl, carboxyl or carboxylic ester,
$R_{17}$ is amino($C_{1-4}$)alkyl, ($C_{1-4}$)alkylamino($C_{1-4}$)alkyl or di($C_{1-4}$)alkylamino($C_{1-4}$)alkyl,
$R_{18}$ is hydrogen or ($C_{1-4}$)alkyl,
$R_{19}$ is hydroxy($C_{1-4}$)alkyl,
$R_{20}$ is ($C_{1-4}$)alkyl or hydroxy($C_{1-4}$)alkyl,
m is 0 to 4,
n is 2 to 8,
o is 0 to 4,
p is 0 to 4,
q is 1 to 8,
r is 0 to 4,
s is 1 to 4,
t is 1 to 4,
u is 1 to 6 and
w is 1 to 6.

In another aspect the present invention provides a compound of formula I, wherein
$R_1$ is chloro or trifluoromethyl,
$R_2$ is hydrogen or trifluoromethyl,
$R_3$ is chloro, fluoro or trifluoromethyl,
$R_4$ is hydrogen, ($C_{1-4}$)alkyl, e.g. methyl, hydroxy($C_{1-4}$)alkyl, e.g. hydroxyethyl, or a group of formula
—CO—$R_5$,
—CO—$(CH_2)_m$—$OR_6$,
—CO—CO—$R_7$,
—CO—CO—$OR_8$,
—CO—N($R_9R_{10}$),
—CO—$(CH_2)_n$—CO—$R_{11}$,
—CO—$(CHR_{15})$—O—$(CH_2)_o$—CO—$R_{11}$,
—CO—$(CH_2)_p$—O—$(CH_2)_q$—O—$(CH_2)_r$—$R_{16}$,
—CO—O—$(CH_2)_s$—O—CO—$R_{17}$,
—CO—O—$(CH_2)_t$—N($R_{18}R_{19}$),
—CO—O—$(CH_2)_u$—NH—CO—CH($NH_2$)—$R_{20}$, or
—CO—O—$(CH_2)_w$—NH—CO—$R_{17}$, wherein
$R_5$ is hydrogen, ($C_{1-4}$)alkyl, ($C_{3-6}$)cycloalkyl, dimethylamino, phenyl or heterocyclyl which is a 6-membered heterocyclic ring system having one O as a heteroatom, e.g. tetrahydropyranyl,
$R_6$ is hydrogen, ($C_{1-4}$)alkyl, ($C_{1-2}$)alkyl substituted by heterocyclyl which is a 5 or 6-membered heterocyclic ring system having 1 or 2 heteroatoms selected from N or O, e.g. including unsubstituted pyrrolidine, morpholine and piperazine and piperazine substituted by e.g. ($C_{1-2}$)alkyl or ($C_{1-2}$)hydroxyalkyl; amino($C_{1-4}$)alkyl, ($C_{1-2}$)alkylamino($C_{1-4}$)alkyl, di($C_{1-2}$)alkylamino($C_{1-4}$)alkyl, hydroxy($C_{1-3}$)alkyl, hydroxy($C_{1-2}$)alkylamino($C_{1-2}$)alkyl or an amino acid residue, e.g. —$CH_2$—CH($NH_2$)—COOH,
$R_7$ and $R_8$ independently of each other are ($C_{1-2}$)alkyl or phenyl,
$R_9$ and $R_{10}$ independently of each other are hydrogen or ($C_{1-2}$)alkyl, $R_{11}$ is $(C_{1-2})$alkyl, $-OR_{12}$, $-NR_{13}R_{14}$, an amino acid, an $(C_{1-2})$alkylester thereof or an di$(C_{1-2})$alkylester thereof, preferably an amino acid selected from the group consisting of alanine, phenylalanine, glutamic acid and lysine, wherein the binding is effected via the α-amino group or in the case of e.g. lysine via the ε-amino group, $R_{12}$ is hydrogen or $(C_{1-2})$alkyl, $R_{13}$ and $R_{14}$ independently of each other are hydrogen, $(C_{1-2})$alkyl, amino$(C_{1-4})$alkyl, $(C_{1-2})$alkylamino$(C_{1-4})$alkyl, di$(C_{1-2})$alkylamino$(C_{1-4})$alkyl, $R_{15}$ is hydrogen or $(C_{1-2})$alkyl, $R_{16}$ is hydrogen, $(C_{1-2})$alkyl, carboxyl or carboxylic ester, $R_{17}$ is amino$(C_{1-2})$alkyl, $R_{18}$ is hydrogen or $(C_{1-2})$alkyl, $R_{19}$ is hydroxy$(C_{1-2})$alkyl, $R_{20}$ is $(C_{1-2})$alkyl or hydroxy$(C_{1-2})$alkyl, m is 0 or 1, n is 2 to 4, o is 0 or 1, p is 0 to 2, q is 2 to 5, r is 0 to 2, s is 2, t is 2, u is 1 to 3 and w is 1 to 3.

In another aspect the present invention provides a compound of formula I, selected from the group consisting of N-[4-(3-Chloro-phenyl)-pyrimidin-2-yl]-N-(4-chloro-3trifluoromethyl-phenyl)-amine, N-[4-(3-Trifluoromethyl-phenyl)-pyrimidin-2-yl]-N-(4-fluoro-3-trifluoromethyl-phenyl)-amine, N-[4-(3-Trifluoromethyl-phenyl)-pyrimidin-2-yl]-N-(4-chloro-3-trifluoromethyl-phenyl)-amine, N-[4-(3-Trifluoromethyl-phenyl)-pyrimidin-2-yl]-N-(4-trifluoromethyl-phenyl)-amine, and N-[4-(3Chloro-phenyl)-pyrimidin-2-yl]-N-(4-trifluoromethyl-phenyl)-amine, wherein the amine group is further substituted by $R_4$, wherein $R_4$ is as defined above.

In a further aspect the present invention provides a compound of formula I wherein $R_1$ is chloro, $R_2$ is hydrogen, $R_3$ is trifluoromethyl and $R_4$ is hydrogen.

In a further aspect the present invention provides a compound of formula I wherein $R_1$ is chloro, $R_2$ is hydrogen, $R_3$ is trifluoromethyl and $R_4$ is a group of formula $-CO-O-(CH_2)_2-N[(C_2H_5OH)(CH_3)]$.

If not otherwise defined herein aryl includes phenyl. Halogen includes fluoro, chloro, bromo. Haloalkyl includes halo$(C_{1-4})$alkyl, wherein halo is one or more halogen, preferably trifluoromethyl. $(C_{3-8})$cycloalkyl includes e.g. $(C_{3-6})$cycloalkyl. Amino includes amino, $(C_{1-4})$alkylamino and di$(C_{1-4})$alkylamino. Aminoalkyl includes amino$(C_{1-6})$alkyl, e.g. $(C_{1-4})$alkylamino$(C_{1-6})$alkyl, di$(C_{1-4})$alkylamino$(C_{1-6})$alkyl, preferably disubstituted amino$(C_{1-4})$alkylamino$(C_{1-4})$alkyl, e.g. dimethyl- or diethylamino$(C_{1-4})$alkyl. Hydroxyalkylamino includes hydroxy$(C_{1-6})$alkyl, hydroxy$(C_{1-4})$alkylamino$(C_{1-6})$alkyl, preferably hydroxy$(C_{1-3})$alkyl or hydroxy$(C_{1-2})$alkylamino$(C_{1-2})$alkyl. Amino acid includes all natural and synthetic amino acids, preferably α-amino acids, e.g. alanine, phenylalanine, glycine, glutamic acid and lysine. Amino acid includes one or more of amino acid, e.g. di- or tripeptides. Heterocyclyl includes 5 or 6 membered heterocyclic ring systems having 1 to 4 heteroatoms selected from N, O or S. Preferably the heterocyclyl is a 5 or 6 membered ring system having 1 or 2 heteroatoms selected from N or O. Preferred is pyrrolidine, morpholine and piperazine.

Any group may be unsubstituted or substituted, e.g. substituted by groups as conventional in organic chemistry, e.g. including groups selected from halogen, haloalkyl, alkylcarbonyloxy, alkoxy, hydroxy, amino, alkylcarbonylamino, aminoalkylcarbonylamino, hydroxyalkylamino, aminoalkylamino, alkylamino, dialkylamino, heterocyclyl having 5 or 6 ring members and 1 to 4 heteroatoms selected from N,O,S; $(C_{1-4})$alkylheterocyclyl, wherein heterocyclyl having 5 or 6 ring members and 1 to 4 heteroatoms selected from N,O,S; hydroxy$(C_{1-4})$alkylheterocyclyl, wherein heterocyclyl having 5 or 6 ring members and 1 to 4 heteroatoms selected from N,O,S; carboxyl, $(C_{1-4})$alkylcarbonyloxy, amino$(C_{1-4})$-alkylcarbonyloxy.

Compounds provided by the present invention are hereinafter designated as "compound(s) of the present invention". A compound of the present invention includes a compound in any form, e.g. in free form, in the form of a salt, in the form of a solvate and in the form of a salt and a solvate.

A salt of a compound of the present invention includes a pharmaceutically acceptable salt, e.g. including a metal salt or an acid addition salt. Metal salts include for example alkali or earth alkali salts; acid addition salts include salts of a compound of formula I with an acid, e.g. including inorganic and organic acids, e.g. including pharmaceutically acceptable acids, such as hydrochloric acid, sulfuric acid, methanesulfonic acid, benzenesulfonic acid, p-toluenesulfonic acid, tartaric acid.

A compound of the present invention in free form may be converted into a corresponding compound in the form of a salt; and vice versa. A compound of the present invention in free form or in the form of a salt and in the form of a solvate may be converted into a corresponding compound in free form or in the form of a salt in unsolvated form; and vice versa.

A compound of the present invention may exist in the form of isomers and mixtures thereof; e.g. optical isomers, diastereoisomers, cis-trans conformers. A compound of the present invention may e.g. contain asymmetric carbon atoms and may thus exist in the form of enantiomeres, diastereolsomeres and mixtures thereof, e.g. racemates. E.g. a substitutent attached to an asymmetric carbon atom in a compound of the present invention may be in the R— or in the S-configuration, including mixtures thereof. The present invention includes a compound of the present invention in any isomeric form and in any isomeric mixture.

Any compound described herein, e.g. a compound of the present invention, may be prepared as appropriate, e.g. according to a method as conventional, e.g. or as described herein.

A compound of the present invention wherein the amine group is substituted by phenyl-substituted pyrimidin; and phenyl; and hydrogen may be prepared e.g. according, e.g. analogously, to a method as conventional, preferably according to the following reaction scheme 1:

SCHEME 1

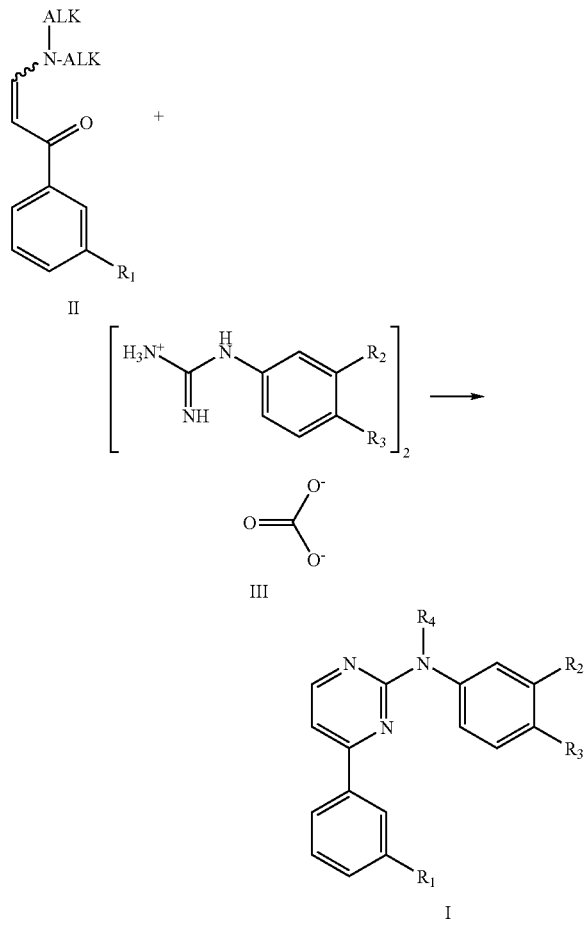

e.g. wherein in a compound of formula I, II and III $R_1$, $R_2$ and $R_3$ are as defined above, and $R_4$ is H; and optionally further reacting a compound obtained with an appropriate reagent to obtain a compound of the present invention, e.g. a compound of formula I, wherein $R_4$ is as defined above, but other than hydrogen; e.g. reacting a compound of formula I wherein $R_4$ is H and the other substituents are as defined above with an alkyliodide in the presence of NaH, to obtain a compound of formula I wherein $R_4$ is alkyl, with a bromo-hydroxyalkane to obtain a compound of formula I wherein $R_4$ is hydroxyalkyl, with a halogenide or an anhydride of a carboxylic acid of formula $R_5$COOH wherein $R_5$ is as defined above, to obtain a compound of formula I wherein $R_4$ is a group —CO—$R_5$, wherein $R_5$ is as defined above, with phosgene to obtain a compound of formula I wherein $R_4$ is —COCl and further reacting a compound obtained with a compound of formula a) $R_6$—$(CH_2)_m$—OH, wherein $R_6$ is as defined above and m is 0 to obtain a compound of formula I wherein $R_4$ is a group of formula —CO—$(CH_2)_m$—$OR_6$, wherein $R_6$ is as defined above and m is 0, b) $R_{17}$—CO—O—$(CH_2)_s$—OH, wherein $R_{17}$ and s are as defined above to obtain a compound of formula I wherein $R_4$ is a group of formula —CO—O—$(CH_2)_s$—O—CO—$R_{17}$, wherein $R_{17}$ and s are as defined above, c) $N(R_{18}R_{19})$—$(CH_2)_t$—OH, wherein $R_{18}$, $R_{19}$ and t are as defined above to obtain a compound of formula I wherein $R_4$ is a group of formula —CO—O—$(CH_2)_t$—$N(R_{18}R_{19})$, wherein $R_{18}$, $R_{19}$ and t are as defined above, d) $R_{20}$—$(NH_2)CH$—CO—NH—$(CH_2)_u$—OH, wherein $R_{20}$ and u are as defined above to obtain a compound of formula I wherein $R_4$ is a group of formula —CO—O—$(CH_2)_u$—NH—CO—CH$(NH_2)$—$R_{20}$, wherein $R_{20}$ and u are as defined above, e) $R_{17}$—CO—NH—$(CH_2)_w$—OH, wherein $R_{17}$ and w are as defined above to obtain a compound of formula I wherein $R_4$ is a group of formula —O—O—$(CH_2)_w$—NH—CO—$R_{17}$, wherein $R_{17}$ and w are as defined above, with a compound of formula $R_5$—CO—Cl, wherein $R_5$ is as defined above to obtain a compound of formula I wherein $R_4$ is a group of formula —CO—$R_5$, wherein $R_5$ is as defined above, with a compound of formula $R_6$—O—$(CH_2)_m$—CO—Cl, wherein $R_6$ is as defined above to obtain a compound of formula I wherein $R_4$ is a group of formula —CO—$(CH_2)_m$—$OR_6$, wherein $R_6$ is as defined above, with a compound of formula $R_7$CO—CO—Cl, wherein $R_7$ is as defined above to obtain a compound of formula I wherein $R_4$ is a group of formula —CO—CO—$R_7$, wherein $R_7$ is as defined above, with a compound of formula $R_8$—O—CO—CO—Cl, wherein $R_8$ is as defined above, to obtain a compound of formula I wherein $R_4$ is a group of formula —CO—CO—$OR_8$, wherein $R_8$ is as defined above, with a compound of formula $(R_9R_{10})N$—CO—Cl, wherein $R_9$ and $R_{10}$ are as defined above, to obtain a compound of formula I wherein $R_4$ is a group of formula —CO—$N(R_9R_{10})$, wherein $R_9$ and $R_{10}$ are as defined above, with a compound of formula $R_{11}$—CO—$(CH_2)_n$—CO—Cl, wherein $R_{11}$, and n are as defined above to obtain a compound of formula I wherein $R_4$ is a group of formula —CO—$(CH_2)_n$—CO—$R_{11}$, wherein $R_{11}$ and n are as defined above, with a compound of formula $R_{11}$—CO—$(CH_2)_o$—O—$(CHR_{16})$—CO—Cl, wherein $R_{11}$, $R_{16}$ and o are as defined above to obtain a compound of formula I wherein $R_4$ is a group of formula —CO—$(CHR_{16})$—O—$(CH_2)_o$—CO—$R_{11}$, wherein $R_{11}$, $R_{16}$ and o are as defined above, with a compound of formula $R_{16}$—$(CH_2)_r$—O—$(CH_2)_q$—O—$(CH_2)_p$—CO—Cl, wherein $R_{16}$, r, q and p are as defined above to obtain a compound of formula I wherein $R_4$ is a group of formula —CO—$(CH_2)_p$—O—$(CH_2)_q$—O—$(CH_2)_r$—$R_{16}$, wherein $R_{16}$, r, q and p are as defined above, with a compound of formula Cl—OC—$(CH_2)_v$—CO—Cl to obtain a compound of formula I wherein $R_4$ is a group of formula —CO—$(CH_2)_v$—CO—Cl and further reacting a compound obtained with an amino acid, an amino acid mono($C_{1-6}$)alkyl ester, an amino acid di($C_{1-6}$)alkyl ester or with a primary or secondary amine, optionally containing additional amine groups to obtain a compound of formula I wherein $R_4$ is a group of formula —CO—$(CH_2)_v$—CO-amino acid, —CO—$(CH_2)_v$—CO- amino acid mono($C_{1-6}$)alkyl ester or —CO—$(CH_2)_v$—CO-amino acid di($C_{1-6}$)alkyl ester and v is 1 to 6, preferably 1 to 5.

Reactions of a compound of formula I wherein $R_4$ is H and the other substituents are as defined above with appropriate reagents to obtain a compound of formula I; wherein $R_4$ is as defined above, but other than hydrogen, are alkylation or acylation reactions and may be carried out as appropriate, e.g. according, such as analogously, to a method as conventional, e.g. or as described above. In such reactions substituents, e.g. hydroxy or amine groups, may be protected before reaction and deprotected during or after reaction.

In another aspect the present invention provides a process for the production of a compound of formula I comprising reacting a compound of formula II wherein $R_1$ is as defined above and ALK denotes alkyl or cycloalkyl, with a compound of formula III, wherein $R_2$ and $R_3$ are as defined above, to obtain a compound of formula I wherein $R_1$, $R_2$ and $R_3$ are as defined above, and $R_4$ is hydrogen, and optionally alkylating or acylating a compound obtained, e.g. and deprotecting groups if desired, to obtain a compound of formula I wherein $R_1$, $R_2$ and $R_3$ are as defined above and $R_4$ is as defined above, but other than hydrogen, and isolating a compound of formula I obtained from the reaction mixture.

Any compound described herein, e.g. a compound of the present invention, may be prepared as appropriate, e.g. according to a method as conventional, e.g. or as described herein. Compounds of formula II and of formula III are known or may be obtained e.g. according to a method as conventional or as described herein.

The compounds of the present invention exhibit in vitro and in vivo pharmacological activity and are therefore useful as pharmaceuticals:

In the course of an allergic response e.g. in the airways, T-helper type 2 cells (Th2 cells) are generated from naïve T-cell precursors following stimulation by allergen presented by dendritic cells (DC) in the presence of the Th2 cytokine IL4. These Th2 cells induce a complex inflammatory response in the lung leading to the onset and progression of allergic asthma. Cytokines produced by these Th2 cells, which include e.g. IL4, IL-5, IL-10 and IL-13, mediate the expansion of pro-inflammatory effector cells such as eosinophils, basophils and mast cells which accumulate in the lungs.

In addition, IL4 and IL-13 induce IgE production by B-cells. Binding of IgE to high affinity IgE receptors (FcεRl) on mast cells and basophils results, following crosslinking by allergen, in the activation of the pro-inflammatory cells and the release of mediators of allergic inflammation.

Based on these observations, it is expected that inhibition of both Th2 cell mediated allergic inflammatory responses and effects on IgE production would provide a novel way to efficiently intervene in allergic asthma and other allergic diseases such as e.g. atopic dermatitis, allergic conjunctivitis and allergic rhinitis.

We have found that the compounds of the present invention may act as modulators of human DC function. DC cell surface molecules known to be important for interaction with naive T-cell precursors, such as CD86, CD83, CD25 and HLA class II antigens may be diminished on the surface of human monocyte-derived dendritic cells upon treatment with compounds of the present invention. Similarly, the secretion of IL-6 by mature DC may be inhibited by the compounds of the present invention. Compound-treated dendritic cells show impaired ability to stimulate the proliferation and cytokine production of naive CD4-positive autologous T-cells.

In addition, we have found that the compounds of the present invention may act as specific inhibitors of IgE synthesis. Upon systemic or oral administration a compound of the present invention may suppress immunoglobulin synthesis, in particular the synthesis of immunoglobulin E in B-lymphocytes, i.e. a compound of the present invention may exhibit isotype specificity. Further we have found that a compound of the present invention may not inhibit B-cell proliferation in concentrations below the concentrations needed to block IgE synthesis.

These activities can be shown in the following assays. Temperature are in degrees Celsius and are uncorrected. The following abbreviations are used:

| | |
|---|---|
| DC | Dendritic cell |
| ELISA | enzyme-linked immunosorbent assay |
| FACS | fluorescence-activated cell sorting |
| FCS | fetal calf serum |
| GM-CSF | granulocyte macrophage-colony stimulating factor |
| IgE | immunoglobulin E |
| IL-4 | interleukin-4 |
| IL-5 | interleukin-5 |
| IL-6 | interleukin-6 |
| IL-10 | interleukin-10 |
| IMDM | Iscove's modified Dulbecco medium |
| KLH | keyhole limpet hemocyanin |
| Mo-DC | monocyte derived dendritic cells |
| PBMC | peripheral blood mononuclear cells |
| SRBC | sheep red blood cells |
| RT | room temperature |
| Th | T helper cell |
| Th2 | T helper cell type 2 |

1. Isotype Specificity:

Inhibition of immunoglobulin synthesis induced in primary human B-lymphocytes stimulated by cytokines and anti-CD40 antibody Mononuclear cells are purified from normal human spleens. The resulting cell suspension contains 50-70% B-lymphocytes as judged by CD19 expression in a FACS analysis. Using 96-well round-bottomed microliter plates (Costar) $5 \times 10^4$ spleenocytes are set up in a final volume of 200 μl/well in IMDM. After pre-incubation with test compound for one hour the cells are cultured to induce IgE production for 9 days at 37° in air supplied with 5% $CO_2$ in the presence of 50 ng/ml of IL-4 and 500 ng/ml of anti-CD40 antibody. The culture cell supernatants are collected and quantitated for IgE by standard isotype specific sandwich ELISA. For the induction of IgG synthesis, the cells are cultured with 100 ng/ml IL-10 and 500 ng/ml of anti-CD40 antibody for the same time period before IgG levels are quantitated in the cell supernatants by isotype specific ELISA.

In these tests the compounds of the present invention inhibit IgE production preferentially over IgG (IgG1).

2. B-Cell Proliferation

Normal human lymphocytes are purified from tonsils by removing contaminating T-cells with SRBC-rosetting according to M. S. Weiner et al., Blood 42 (1973) 939. The resulting B-cells are more than 95% pure as judged by CD19 expression in a FACS analysis. Using 96-well round-bottomed microliter plates (Costar) $1 \times 10^5$ spleenocytes are set up in a final volume of 200 μl/well in IMDM. After pre-incubation with test compound for one hour, cell proliferation is induced with 50 ng/ml IL-4 and 500 ng/ml anti-CD40 antibody. After a 4 day incubation period at 37° in air supplied with 5% $CO_2$, 1 μCl of tritiated thymidine is added and the cells are cultured for ca. 16 hours. The cells are collected on a nitrocellulose filter and the DNA-bound radioactivity is quantitated by liquid scintillation counting.

In these tests compounds of the present invention inhibit IL-4 and anti-CD40 antibody mediated B-cell proliferation above the concentrations needed to block IgE synthesis.

3. Modulation of DC Cell Surface Markers

Human peripheral blood monocytes are prepared by elutriation or by negative selection of PBMC using a commercially available kit (Miltenyi). The resulting monocyte population is routinely >97% positive for CD14 as checked for purity by FACS staining for CD14. Monocytes are seeded in 6-well plates at $3 \times 10^6$ cells/well in 5ml of IMDM medium supplemented with 1% FCS, streptomycin and glutamin. Generation of immature Mo-DC is induced by adding 40 ng/ml IL-4 and 15 ng/ml GM-CSF for 6 days in the absence or presence of test compounds. After the first 2 days, half of the volume is replaced with fresh medium, cytokines and compounds where appropriate. On day 6 of culture, cell surface expression levels of CD86 and HLA-DR is measured by FACS staining.

Maturation of DC is induced by activation of immature DC with 100 ng/ml LPS (Sigma) or by a cocktail containing 20 ng/ml GM-CSF, 100 U/ml IFN-γ, 20 U/ml TNF-α and 4 μg/ml crosslinked anti-CD40 monoclonal antibodies for 24 hours. Then, cell surface expression levels of CD83 and CD25 was quantitated by FACS.

In these tests, compounds of the present invention inhibit the cell surface expression levels of CD86, HLA-DR, CD83 and CD25.

4. DC Mediated Antigen Specific Autologous T-Cell Stimulation Assay

Immature Mo-DC are generated in the absence or presence of test compounds. Then, the cells are pulsed with 100 μg/ml KLH over night and then co-cultured with autologous CD4-positive T-cells for nine days to elicit a primary T-cell response in the absence or presence of test compound. After washing the cells, the primed T-cells are re-stimulated with fresh KLH-pulsed DC in different T/DC ratios for 3 days without adding compound. For the last 16 hours 1 μCl of tritiated thymidine is added. The cells are collected on a nitrocellulose filter and the DNA-bound radioactivity is quantitated by liquid scintillation counting. In these tests, compounds of the present invention inhibit DC mediated T-cell proliferation.

5. T-Cell Cytokine Production

Supernatants from DC/T-cell re-stimulation cultures (see above) were taken after 48 hours and quantitated for GM-CSF and IL-2 by ELISA using commercially available kits. In these tests, compounds of the present invention inhibit DC mediated T-cell cytokine production.

6. Determination of Stability of Compounds of the Present Invention in Plasma Heparinized blood is obtained from human volunteers and from Balb/c mice. Blood obtained is centrifuged for 4 minutes at 13,000 rpm at room temperature (RT) to obtain plasma. To aliquots of plasma (1 ml) test compounds, i.e. compounds of the present invention, are added (1 μl of 10 mM stock solutions in DMSO or water). The samples are incubated at 37°. At various time points, aliquots of 100 μl are taken from said samples. An internal standard (5 μl of a 100 μg/ml solution of an internal standard compound in methanol) is added, followed by 300 μl of methanol (or acetonitrile or acetonitrile/1 M HCl, as required). Samples are centrifuged for 5 minutes at 13,000 rpm.

For analysis, 50 μl of the supernatants obtained are injected into an HPLC system (HP1090), equipped with a Hypersil BDS C-8 column (5 μm, 250×4.6 mm) plus pre-column (10× 4.6 mm). The column is eluted isocratically at 55° C. and at a flow rate of 1.5 ml/min with mixtures of acetonitrile and 10 mM $(NH_4)_2SO_4$, pH 2.7; the acetonitrile content of the mixtures used is in the range of 55-65% for various substances.

Analysis of specific compounds may require a different HPLC-system, e.g. column: Zorbax Extend C18 (3.5 μm, 150×4.6 mm); pre-column: Hypersil BDS, C-8 (5 μm, 10×4.6 mm); RT; acetonitrile contents of solvent: 65%.

UV detection is carried out at 277 nm. For calibration, plasma samples are spiked with a compound of formula I wherein $R_4$ Is hydrogen, or with a compound of formula I wherein $R_4$ is as defined above, but other than hydrogen; both in the range of 0.5 to 20 μM, and internal standard. Absolute concentrations are calculated using these calibration sets.

In these determination tests we have found that a compound of formula I wherein $R_4$ is as defined above, but other than hydrogen has a lower stability in plasma than a compound of formula I wherein $R_4$ is hydrogen. From that it may be assumed that compounds of formula I wherein $R_4$ is as defined above, but other than hydrogen, may be regarded as prodrugs of compounds of formula I, wherein $R_4$ is hydrogen. Compounds of formula I, wherein $R_4$ is hydrogen, on the other hand, may establish a highly active principle, e.g. may establish the basic structure for the surprising activity of a compound of the present Invention which was found in vitro and in vivo. Compounds of formula I, wherein $R_4$ is hydrogen may thus be regarded as those compounds having the regular drug structure.

Compounds of the present invention show a good solubility and good plasma levels after e.g. oral administration.

The compounds of the present invention are therefore indicated for use as modulators of DC function and inhibitors of immunoglobulin synthesis, especially inhibitors of IgE synthesis, and are useful in the treatment of IgE-mediated diseases, particularly IgE-mediated allergic diseases, e.g. of diseases mediated by IgE expression, such as a topic dermatitis, particularly in children, urticaria, particularly acute urticaria, allergic asthma, allergic rhinitis, food allergies, allergic conjunctivitis, hayfever, bullous pemphigoid and, industrial sensitization. In addition, these compounds are indicated in other diseases in which inflammatory conditions play a major pathological role, such as autoimmune diseases (e.g. systemic lupus erythematosus, psoriasis and rheumatoid arthritis) and gastrointestinal diseases (e.g. Crohns disease) and chronic rejection of transplants.

In another aspect the present invention provides the use of an amine, which is substituted by
  phenyl-substituted pyrimidin; and
  phenyl; and
  a third substituent, e.g. a compound of the present invention, in the preparation of a medicament for the treatment of IgE-synthesis-mediated diseases, autoimmune diseases, gastrointestinal diseases and chronic rejection of transplants. A third substituent e.g. includes a group $R_4$ as defined above.

In a preferred aspect the present invention provides the use of a compound of formula I wherein the substituents $R_1$ to $R_4$ are as defined above in the preparation of a medicament for the treatment of IgE-synthesis-mediated diseases, autoimmune diseases, gastrointestinal diseases and chronic rejection of transplants.

For the above uses the dosage to be used will vary, of course, depending e.g. on the particular compound employed, the mode of administration and the treatment desired. However, in general satisfactory results may be obtained when the compounds are administered at a daily dosage of from about 1 mg/kg to about 30 mg/kg animal body weight, suitably given in divided doses two to four times daily. For most larger mammals the total daily dosage is from about 70 mg to about 2000 mg, conveniently administered, for example, in divided doses up to four times a day or in retard form. Unit dosage forms comprise, for example, from about 17.5 mg to about 1000 mg of compound in admixture with at least one solid or liquid, pharmaceutically acceptable excipient, e.g. carrier or diluent.

A compound of the present invention may be administered in similar manner to known standards such as glucocorticoids and antihistaminics for use in such indications. It may be admixed with conventional therapeutically acceptable carriers and diluents and, optionally, further excipients, and administered e.g. orally in such forms, e.g. in the form of tablets, capsules; or, alternatively, it may be administered topically, e.g. in conventional forms, such, as aerosols, ointments or creams; parenterally or intravenously. The concentration of the substance will, of course vary, e.g. depending on the compound administered, the treatment desired and the nature of the form. In general, however, satisfactory results may be obtained in topical application forms at concentrations of from about 0.05% to about 5%, particularly from about 0.1% to about 1% by weight.

In another aspect the present invention provides the use of a compound of the present invention in the preparation of a medicament for the therapy of IgE-mediated diseases, e.g. of diseases mediated by IgE expression, autoimmune diseases, gastrointestinal diseases and chronic transplant rejection.

Pharmaceutical compositions for use in the therapy of IgE-mediated diseases, autoimmune diseases, gastrointestinal diseases and chronic transplant rejection may be prepared by mixing a compound of the present invention together with at least one pharmaceutically acceptable excipient, e.g. carrier or diluent.

In another aspect the present invention provides a method of treatment of IgE-mediated diseases, autoimmune diseases, gastrointestinal diseases and chronic transplant rejection which comprises administering a therapeutically effective amount of a compound of the present invention, e.g. in the form of a pharmaceutical composition, to a subject in need of such treatment.

A compound of the present invention may be well tolerated, as may be determined according to a method as conventional. A compound of the present invention may possess beneficial pharmacogalenical properties, such as good solubility in various solvents.

In another aspect the present invention provides a compound of the present invention for use as a pharmaceutical, preferably in indications of IgE mediated diseases, autoimmune diseases, gastrointestinal diseases and chronic transplant rejection.

The compounds of the present invention may be administered in the form of a pharmaceutically acceptable salt, e.g. an acid addition salt or metal salt; or in free form; optionally in the form of a solvate. The compounds of the present invention in the form of a salt exhibit the same order of activity as the compounds of the present invention in free form; optionally in the form of a solvate.

In another aspect the present invention provides a pharmaceutical composition comprising a compound of the present invention in association with at least one pharmaceutical excipient, e.g. carrier or diluent. Such compositions may be manufactured according to a method as conventional.

A compound, or more than one compounds, of the present invention may be used for pharmaceutical treatment according to the present invention alone, or in combination with one or more other pharmaceutically active agents, e.g. such as useful in the treatment of IgE-mediated diseases, particularly IgE-mediated allergic diseases, e.g. of diseases mediated by IgE expression, such as atopic dermatitis, particularly in children, urticaria, particularly acute urticaria, allergic asthma, allergic rhinitis, food allergies, allergic conjunctivitis, hayfever, bullous pemphigoid and industrial sensitization. In addition, these compounds are indicated in other diseases in which inflammatory conditions play a major pathological role, such as autoimmune diseases (e.g. systemic lupus erythematosus, psoriasis and rheumatoid arthritis) and gastrointestinal diseases (e.g. Crohns disease) and chronic rejection of transplants. Such other pharmaceutically active agents include e.g. steroids, anti-histaminica, ascomycins, ASM981, rapamycins.

Combinations include fixed combinations, in which two or more pharmaceutically active agents are in the same formulation; kits, in which two or more pharmaceutically active agents in separate formulations are sold in the same package, e.g. with instruction for co-administration; and free combinations in which the pharmaceutically active agents are packaged separately, but instruction for simultaneous or sequential administration are given.

In another aspect the present invention provides a pharmaceutical composition comprising as an active ingredient a compound of the present invention in combination, e.g. including fixed combinations, kits and free combinations, with one or more other pharmaceutically active agents, e.g. which other pharmaceutically active agents are, e.g. selected from, e.g. the group consisting of, steroids, anti-histaminica, ascomycins, ASM981, rapamycins.

In the following examples which illustrate the invention references to temperature are in degrees Celsius and are uncorrected. In the $^1$H-NMR chemical shifts are given in delta units; J values in Hz The following abbreviations are used:

| m.p. | melting point |
| RT | room temperature |
| br. | broad |

EXAMPLE 1

N-[4-(3-Chloro-phenyl)-pyrimidin-2-yl]-N-(4-trifluoromethyl-phenyl)-amine

A) 1-(3-Chloro-phenyl)-3-dimethylamino-propenone

A mixture of 50 g of 3-chloroacetophenone and 65 ml of N,N-dimethylformamide dimethyl acetal is heated at ca. 100° for ca. 24 hours and cooled to RT. A precipitate formed is filtrated off, washed and dried. 40 g of 1-(3-chloro-phenyl)-3-dimethylamino-propenone in crystalline form are obtained. m.p. 72.8°.

B) N-(4-Trifluoromethyl-phenyl)-quanidine carbonate 13.75 ml of aqueous 37% HCl are added dropwise to a mixture of 17.5 ml of 4-trifluoromethylaniline and 28 ml of water, the mixture obtained is preheated to ca. 75° for ca. 20 minutes. To the mixture obtained a solution of 12.9 g of cyanamide in 13 ml of water is added dropwise at ca. 75° and stirring is continued for ca. 4 hours at that temperature. The mixture obtained is cooled to RT and a solution of 9.26 g of Na$_2$CO$_3$ in 43 ml of water are added dropwise. To the mixture obtained 140 ml of water are added and the mixture obtained is stirred overnight. A solid precipitates, is filtrated off, washed and dried. 14 g of N-(4-trifluoromethyl-phenyl)-guanidine carbonate in crystalline form are obtained. m.p. 125.3°.

C) N-[4-(3Chloro-phenyl)-pyrimidin-2-yl]-N-(4-trifluoromethyl-phenyl)-amine

A mixture of 1.5 g of 1-(3-chloro-phenyl)-3-dimethy-lamino-propenone, 1.7 g of of N-(4-trifluoromethyl-phenyl)-guanidine carbonate and 15 ml of n-butanol is heated at 120° for ca. 24 hours, the mixture obtained is cooled to RT and a solid precipitates. The precipitate is filtrated off and is recrystallised from n-butanol. 1.0 g of N-[4-(3-chlorophenyl)-pyrimidin-2-yl]-N-(4-trifluoromethyl-phenyl)amine in crystalline form are obtained. m.p. 201.5°.

Analogously as described in example 1 but using appropriate starting material, compounds of formula

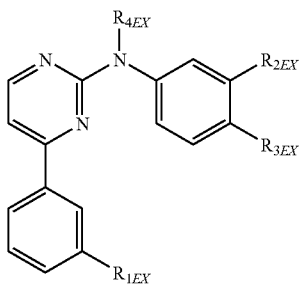

$I_{EX}$ wherein $R_{1EX}$, $R_{2EX}$ and $R_{3EX}$ are as defined in TABLE 1 below and $R_{4EX}$ is H, having a melting point m.p. as defined in TABLE 1 below are obtained:

TABLE 1

| Example | $R_{1EX}$ | $R_{2EX}$ | $R_{3EX}$ | m.p. (°) |
|---|---|---|---|---|
| 2 | $CF_3$ | $CF_3$ | F | 168.0 |
| 3 | Cl | $CF_3$ | Cl | 182.3 |
| 4 | $CF_3$ | $CF_3$ | Cl | 161.8 |
| 5 | $CF_3$ | H | $CF_3$ | 185.9 |

Starting from a compound of formula

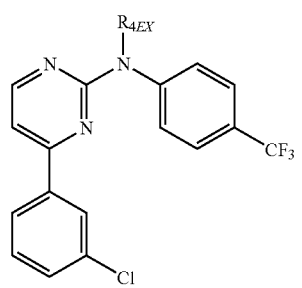

$II_{EX}$ wherein $R_4$ is hydrogen, which is the compound N-[4-(3-chloro-phenyl)-pyrimidin-2-yl]-N-(4-trifluoromethyl-phenyl)-amine, compounds of the following examples 6 to 68, wherein $R_4$ is as defined in said examples, may be obtained.

EXAMPLE 6

Compound of formula $II_{Ex}$, wherein $R_{4EX}$ is a group of formula —CO—CH$_3$N-[4-(3-Chloro-phenyl)-pyrimidin-2-yl]-N-(4-trifluoromethyl-phenyl)-acetamide A solution of 1.6 g of a compound of formula $II_{EX}$ wherein $R_4$ is hydrogen and 300 mg of 4-dimethylaminopyrimidine in 30 ml of dry pyridine is treated with acetic acid anhydrid and stirred at 70°. From the mixture obtained solvent is evaporated off, diethyl ether is added and a precipitate obtained is removed by filtration. The filtrate obtained is concentrated and the concentrate obtained is subjected to silicagel medium pressure chromatography. N-[4-(3-Chloro-phenyl)-pyrimidin-2-yl]-N-(4-trifluoromethyl-phenyl)-acetamide is obtained in solid (crystalline) form from a mixture of toluene and pentane in the form of a powder. m.p. 128.6-129.6°.

Analogously to the method as described in example 6, but using appropriate starting materials, compounds of formula $II_{EX}$, wherein $R_{4EX}$ is as set out in TABLE 2 below, having $^1$H-NMR or m.p. data as defined in TABLE 2 are obtained:

TABLE 2

| Example | $R_{4EX}$ | m.p./$^1$H-NMR |
|---|---|---|
| 7 | —CO—CH$_2$—CH$_3$ | 121.1° |
| 8 | —CO—CH(CH$_3$)$_2$ | 122-122.8° |
| 9 | —CO—C$_6$H$_5$ | 130.1° |
| 10 | —CO—CH$_2$—CH(CH$_3$)$_2$ | 109-110° |
| 11 | —CO—CO—C$_6$H$_5$ | 144.9° |
| 12 | —CO—C(CH$_3$)$_3$ | 103.9-104.7° |
| 13 | —CO—cyclohexyl | 136.8° |
| 14 | —CO—tetrahydropyranyl | 158.8° |
| 15 | —CO—CO—O—CH$_2$—CH$_3$ | 133.7° |
| 16 | —CO—CH$_2$—O—CO—CH$_3$ | 150.8° |
| 17 | —CO—CO—O—CH$_3$ | 141.3° |
| 18 | —CO—cyclopropyl | 94.5-95.8° |
| 19 | —CO—CH$_2$—O—CH$_3$ | 124.6° |
| 20 | (chiral lactate ester structure) | $^1$H-NMR (d$_6$-DMSO, 400 MHz, RT): 8.96 (d, J=5.3, 1H), 8.15 (d, J=5.3, 1H), 7.95 (d, J=8.3, 2H), 7.70 (t, J=7.8, 1H), 7.60 (d, J=8.2, 2H), 5.97 (q, J=6.7, 1H), 2.06 (s, 3H), 1.69 (d, J=6.7, 3H) |

EXAMPLE 21

Compound of formula II$_{EX}$, wherein R$_{4EX}$ is a group of formula

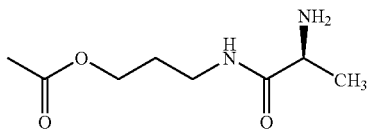

4-(3-Chloro-phenyl)-pyrimidin-2-yl]-(4-trifluoromethyl-phenyl)-carbamic acid 3-((S)-2-tert.-butoxycarbonylamino-propionylamino)-propyl ester in the Form of a Free Base and in the Form of a Hydrochloride 0.5 g of a solution of a compound of formula II$_{EX}$ wherein R$_4$ is hydrogen in 30 ml of dry chlorobenzene is treated with a solution of 0.76 ml of 20% phosgene in toluene. The mixture obtained is stirred at 130°, a clear solution obtained is cooled to 100° and a further solution of 0.76 ml of 20% phosgene in toluene is added. The mixture obtained is stirred at 130°, cooled to 100° and treated with argon in order to remove excess phosgene. To the mixture obtained a solution of 144 µl of [(S)-1-(3-hydroxy-propylcarbamoyl)-ethyl]-carbamic acid tert-butyl ester and 130 µl of pyridine in 5 ml of chlorobenzene is added, the mixture obtained is stirred at 130° and cooled to RT. The mixture obtained is washed with 1N aqueous HCl, aqueous, saturated NaHCO$_3$ solution and brine and concentrated. The concentrate obtained is subjected to flash chromatography on silicagel. [4-(3-Chloro-phenyl)-pyrimidin-2-yl]-(4-trifluoromethyl-phenyl)-carbamic acid 3-((S)-2-tert.-butoxycarbonylamino-propionylamino)-propyl ester is obtained in the form of an oil.

$^1$H-NMR (CDCl$_3$, 400 MHz, RT) δ: 8.77(d;1H), 7.94(s; 1H), 7.83(d;1H), 7.69(d;1H), 7.51(d; 1H), 7.50-7.38(m;4H), 4.35(t;2H), 3.16(m;2H), 1.84(m;2H), 1.43(s;9H).

276 mg of a solution of [4-(3-chloro-phenyl)-pyrimidin-2-yl]-(4-trifluoromethyl-phenyl)-carbamic acid 3-((S)-2-tert.-butoxycarbonylamino-propionylamino)-propyl ester in trifluoroacetic acid is stirred for ca. 2 hours. From the mixture obtained solvent is evaporated off and the evaporation residue obtained is dissolved in diethyl ether. The mixture obtained is treated with HCl in diethyl ether. [4-(3—Chloro-phenyl)-pyrimidin-2-yl]-(4-trifluoromethyl-phenyl)-carbamic acid 3-((S)2-tert.-butoxycarbonylamino-propionylamino)-propyl ester in the form of a hydrochloride precipitates, is filtrated off, washed and dried. m.p.: 54.6-54.8°.

Analogously to the method as described in example 21, but using appropriate starting materials, compounds of formula II$_{EX}$, wherein R$_{4EX}$ is as described in TABLE 3 below, having $^1$H-NMR or m.p. data as defined in TABLE 3 are obtained:

TABLE 3

| Example | R$_{4EX}$ | m.p./$^1$H-NMR |
|---|---|---|
| 22 | (structure: acetoxy-propyl-NH$_2$) | 65.7-72.9° |
| 23 | (structure: acetoxy-CH$_2$-CH(NH$_2$)-CH$_3$) | 192.5-194.2° |
| 24 | (structure: acetoxy-ethyl-NH-ethyl-OH) | 191.9-193.7° |
| 25 | (structure: acetoxy-methyl-pyrrolidine) | 126.8-130.8° |
| 26 | (structure: acetoxy-ethyl-NH$_2$) | 161-162.8° |
| 27 | (structure: acetoxy-CH$_2$-CH(NH$_2$)-COOH) | 138.1-143.2° |
| 28 | (structure: acetoxy-ethyl-O-CO-CH(NH$_2$)-CH$_3$) | $^1$H-NMR (d$_6$-DMSO, 400 MHz, RT) δ: 8.86 (d; 1H), 8.44 (bd; 3H), 8.15 (m; 1H), 8.10 (m; 1H), 8.06 (d; 1H), 7.76/7.51 (AB-system; 4H), 7.64 (m; 1H), 7.57 (t; 1H), 4.62-4.36 (m; 3H), 4.32-4.28 (m; 1H), 4.02-3.98 (m; 1H), 1.26 (d; 3H) |

TABLE 3-continued

| Example | R$_{4EX}$ | m.p./$^1$H-NMR |
|---|---|---|
| 29a | (structure: acetoxyethyl-NH-C(=O)-CH(NH$_2$)-CH$_3$) | 133-136.3° |
| 29b | as in example 29a | 185.6-187.1° |
| 30 | (structure: acetoxyethyl-NH-C(=O)-CH(NH$_2$)-CH(OH)-CH$_3$) | 91.9-95° |
| 31 | (structure: acetyl-O-CH$_2$CH$_2$CH$_2$-O-C(=O)-CH(NH$_2$)-CH$_3$) | $^1$H-NMR (d$_6$-DMSO): 8.85 (d; 1H), 8.23 (br; 2H), 8.14 (m; 1H), 8.10 (m; 1H), 8.06 (d; 1H), 7.76 (d; 2H), 7.64 (m; 1H), 7.59 (t; 1H), 7.49 (d; 2H), 4.28 (m; 2H), 4.12 (m; 2H), 4.07 (q, 1H), 1.93 (m; 2H), 1.34 (d; 3H) |

In TABLE 3 the m.p. or $^1$H-NMR data is the data of the compounds of examples 22 to 28, 29a and 30 in the form of hydrochlorides, for example 29b in the form of the besylate and for example 31 in the form of the trifluoroacetate.

EXAMPLE 32a

Compound of formula II$_{EX}$, wherein R$_{4EX}$ is a group of formula

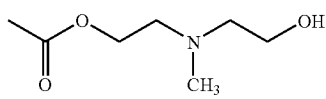

[4-(3-Chloro-phenyl)-pyrimidin-2-yl]-(4-trifluoromethyl-phenyl)-carbamic acid 2-[(2-hydroxy-ethyl)-methyl-amino]-ethyl ester in the Form of a Hydrochloride 0.5 g of a solution of a compound of formula II$_{EX}$ wherein R$_4$ is hydrogen in 30 ml of dry chlorobenzene is treated with a solution of 0.76 ml of 20% phosgene in toluene. The mixture obtained is stirred at 130°, a clear solution obtained is cooled to 100° and a further solution of 0.76 ml of 20% phosgene in toluene is added. The mixture obtained is stirred at 130°, cooled to 100° and treated with argon in order to remove excess phosgene. The mixture obtained is treated at RT with 0.675 ml of a solution of 2-[(2-hydroxy-ethyl)methyl-amino]-ethanol in 5 ml of chlorobenzene and stirred at 130°, cooled to RT and concentrated in vacuum. The concentration residue obtained is dissolved in ethyl acetate and washed with aqueous, saturated NaHCO$_3$ solution and brine. The organic layer obtained is treated with acetic acid, the mixture obtained is concentrated in vacuum and the concentrate obtained is subjected to chromatography. [4-(3-Chlorophenyl)-pyrimidin-2-yl]-(4-trifluoromethyl-phenyl)-carbamic acid 2-[(2-hydroxy-ethyl)-methyl-amino]-ethyl ester in the form of an acetate obtained is dissolved in diethylether and treated with HCl in diethyl ether. [4-(3-Chloro-phenyl)-pyrimidin-2-yl]-(4-trifluoromethyl-phenyl)-carbamic acid 2-[(2-hydroxy-ethylmethyl-amino]-ethyl ester in the form of a hydrochloride precipitates (crystallizes), is filtrated off, washed and dried. m.p.: 145.9-147.7°.

Analogously to the method as described in example 32a, but using appropriate starting materials, compounds of formula II$_{EX}$, wherein R$_{4EX}$ is as described in TABLE 4 below, having $^1$H-NMR or m.p. data as defined in TABLE 4 are obtained:

TABLE 4

| Example | R$_{4EX}$ | m.p./$^1$H-NMR |
|---|---|---|
| 32b | as in example 32a | 119.5° |
| 32c | as in example 32a | 190.2-190.7° |
| 32d | as in example 32a | 66.5-72.2° |
| 32e | as in example 32a | 134.1-135.5° |
| 32f | as in example 32a | 130.4-132.5° |
| 33 | —CO—O—CH$_2$—CH$_3$ | 68.3-69.2° |

TABLE 4-continued

| Example | $R_{4EX}$ | m.p./$^1$H-NMR |
|---|---|---|
| 34 | (acetate-O-CH₂CH₂-morpholine) | 151.3-154.3° |
| 35 | (acetate-O-CH₂CH₂-pyrrolidine) | 171.2-174.3° |
| 36 | (acetate-O-CH₂CH₂CH₂-N(CH₃)₂) | 128.9-129.1° |
| 37 | (acetate-O-CH₂CH₂CH₂-OH) | $^1$H-NMR (DMSO-d6, 400 MHz, RT) δ: 8.85 (d; 1H), 8.15 (m; 1H), 8.10 (m; 1H), 8.04 (d; 1H), 7.75/7.48 (AB-system, 4H); 7.63 (m; 1H), 7.57 (t; 1H), 4.46 (t; 1H), 4.25 (t; 2H), 3.34 (dt; 2H), 1.69 (d; 2H) |
| 38 | (acetate-O-CH₂CH₂-N(CH₃)₂) | 152.7-156.2° |
| 39 | (acetate-O-CH₂CH₂-piperazine-CH₂CH₂OH) | 154.9-162.8° |
| 40 | (acetate-O-CH₂CH₂-piperazine-N-CH₃) | $^1$H-NMR (d₆-DMSO, 400 MHz, RT) δ: 8.86 (d; 1H), 8.11-8.05 (m; 3H), 7.79 (d; 2H); 7.64-7.57 (m; 4H), 4.62 (bs; 2H), 3.60-3.40 (m; 8H), 3.40-3.25 (m; 2H), 2.76 (s; 3H) |

In TABLE 4 the m.p. or $^1$H-NMR data of examples 33, 37 and 40 is the data of the compounds in free base form, the m.p. or $^1$H-NMR data of examples 34, 35, 36, 38 and 39 is the data of the compounds in the form of hydrochlorides, the m.p. of example 32b to 32f) are the date for the following salts: 32b) mesylate, 32c) sulfate, 32d) tartrate, 32e) p-toluenesulfonate and 32f) besylate.

EXAMPLE 41

Compound of formula II$_{EX}$, wherein R$_{4EX}$ is —CH$_3$
[4-(3-Chloro-phenyl)-pyrimidin-2-yl]-methyl-(4-trifluoromethyl-phenyl)-amine A solution of 160 mg of a compound of formula II$_{EX}$ wherein R$_4$ is hydrogen in 4 ml of dry dimethylformamide is treated with NaH, the mixture obtained is stirred at 100°, cooled to RT and treated with 57 μl of methyliodide. The mixture obtained is stirred overnight at RT. From the mixture obtained a precipitate is filtrated off and the filtrate obtained is concentrated in vacuum. The concentration residue obtained is subjected to flash chromatography on silicagel. [4-(3-Chloro-phenyl)-pyrimidin-2-yl]-methyl-(4-trifluoromethyl-phenyl)-amine obtained is precipitated from n-pentane in the form of a solid, filtrated off and dried. Structure confirmed by $^1$H-NMR data.

Analogously to the method as described in example 41, but using appropriate starring materials, compounds of formula II$_{EX}$, wherein R$_{4EX}$ is CH$_3$ is prepared.

EXAMPLE 42

$^1$H-NMR: 8.55 (d, J=5.2 Hz, 1H); 7.49 (d, 1H); 3.59 (s, 3H)

EXAMPLE 43

R$_{4EX}$ is —CO—N(CH$_3$)$_2$

A mixture of 0.5 g of N-[4-(3-chloro-phenyl)-pyrimidin-2-yl-N-(4-trifluoromethyl-phenyl)-amine, 86 mg of NaH, 0.4 ml of N,N-dimethylcarbamoylchloride in 5 ml of N,N-dimethylformamide is heated for 4 hours at 80°. Solvent is evaporated and to a residue obtained ethylacetate is added. After washing and drying a concentrate obtained is chromatographed on silicagel and the product is obtained. m.p. 143°.

EXAMPLE 44

R$_{4Ex}$ is 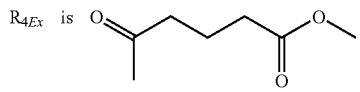

A mixture of 1 g of N-[4-(3-chloro-phenyl)-pyrimidin-2-yl]-N-(4-trifluoromethyl-phenyl)-amine, 1.98 ml of glutaric acid monomethyl ester chloride, 1.1 ml pyridine and 10 mg of dimethylaminopyridine in 25 ml of toluene is heated. The mixture is diluted with ethyl acetate, washed with cold 0.01 N aq HCl, aq. bicarbonate and brine. The organic phase is dried, solvent evaporated and the product is obtained.

(d$_6$-DMSO, 500 MHz, RT): 8.83 (d, J=5.2, 1H); 8.12-8.10 (m, 1H); 8.10-8.07 (m, 1H); 8.02 (d, J=5.2, 1H); 7.79 (d, J=8.5, 2H) 7.65-7.62 (m, 1H); 7.57 (t, J=7.8, 1H); 7.47 (d, J=8.2, 2H); 3.53 (s, 3H); 2.84 (t, J=7.3, 2H); 2.38 (t, J=7.5, 2H); 1.89 (quintett, J=7.3, 2H)

Analogously as described in example 44 but using appropriate starting material, compounds of formula I, wherein R$_{4EX}$ is as described in TABLE 5 below, having $^1$H-NMR (d$_6$-DMSO, 500 MHz, RT, unless given otherwise) or m.p. as defined in TABLE 5 are obtained:

rated. The evaporation residue obtained is filtered and a filtrate obtained is acidified to pH 2 with 0.1 N HCl and extracted with ethylacetate. The organic phase is washed and dried and solvent is stripped off to give a solid. Crystallisation from a mixture dichloromethane and pentane results in the product.

m.p.: 138.6° C. $^1$H-NMR: (d$_6$-DMSO, 500 MHz, RT): 12.01 (br, 1H); 8.83 (d, J=5.2, 1H); 8.10 (m, 1H); 8.09-8.07 (m, 1H); 8.01 (d, J=5.4, 1H); 7.78 (d, J=8.7, 2H); 7.63-7.61 (m, 1H); 7.56 (t, J=7.8, 1H); 7.47 (d, J=8.7, 2H); 2.84 (t, J=7.5, 2H); 2.29 (t, J=7.4, 2H); 1.87 (quintett, J=7.3. 2H)

EXAMPLE 49b 40 mg of calcium hydroxide are added to a mixture of 0.5 g of a compound of example 49a, 11 ml of tetrahydrofuran and 5 ml of water. A mixture obtained is shaken for a few

TABLE 5

| Example | R$_{4EX}$ | m.p./$^1$H-NMR |
|---|---|---|
| 45 | ![structure] | 8.83 (d, J=5.2, 1H); 8.12-8.11 (m, 1H); 8.10-8.08 (m, 1H); 8.02 (d, J=5.2, 1H); 7.78 (d, J=8.5, 2H); 7.65-7.62 (m, 1H); 7.58 (t, J=7.9, 1H); 7.45 (d, J=8.3, 2H); 3.54 (s, 3H); 2.79 (t, J=7.5, 2H); 2.29 (m, 2H); 1.68-1.62 (m, 2H); 1.52-1.48 (m, 2H) |
| 46 | ![structure] | (400MHz): 8.84 (d, J=5.3, 1H); 8.13-8.09 (m, 2H); 8.02 (d, J=5.3, 1H); 7.80 (d, J=8.4, 2H); 7.64-7.62 (m, 1H); 7.57 (t, J=7.8, 1H); 7.46 (d, J=8.2, 2H); 3.59 (s, 3H); 3.12-3.08 (m, 2H); 2.68-2.65 (m, 2H) |
| 47 | ![structure] | 8.77 (d, J=5.5, 1H); 8.08-8.07 (m, 2H); 7.96 (d, J=5.2, 1H); 7.83 (d, J=8.5, 2H); 7.65-7.62 (m, 1H); 7.57 (t, J=8.1, 1H); 7.51 (d, J=8.2, 2H); 4.90 (s, 2H); 4.22 (s, 2H); 3.61 (s, 3H) |
| 48 | ![structure] | 8.79 (d, J=5.5, 1H); 8.11-8.10 (m, 1H); 8.09-8.08 (m, 1H); 7.98 (d, J=5.2, 1H); 7.81 (d, J=8.2, 2H); 7.65-7.62 (m, 1H); 7.58 (t, J=8.1, 1H); 7.47 (d, J=8.2, 2H); 4.72 (s, 2H); 3.56-3.54 (m, 2H); 3.34-3.32 (m, 2H); 3.14 (s, 3H) |

EXAMPLE 49a

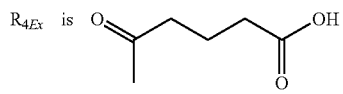

0.01 N aqueous NaOH is added dropwise to a solution of 4.5 g N-[4-(3-chloro-phenyl)-pyrimidin-2-yl]-N-(4-trifluoromethyl-phenyl)-amine in a mixture of tetrahydrofuran and water. A precipitate formed is filtered off and solvent is evapominutes and left at RT. Crystals separated are filtered and washed with cold isopropanol to give the calcium salt of a compound of example 49a.

$^1$H-NMR (d$_6$-DMSO, 400 MHz, RT): 8.83 (d, J=5.3); 8.00 (d, J=5.3); 7.78 (d, J=8.5); 7.45 (d, J=8.3); 2.78 (t, J=7.5); 1.99 (t, J=7.3); 1.8 (m)

Analogously as described in example 49a but using appropriate starting material, compounds of formula I, wherein R$_{4EX}$ is as described in TABLE 6 below, having $^1$H-NMR (d$_6$-DMSO, 500 MHz, RT) or m.p. as defined in TABLE 6 are obtained:

TABLE 6

| Example | R$_{4EX}$ | m.p./$^1$H-NMR |
|---|---|---|
| 50 | (structure) | 11.98 (br, 1H); 8.83 (d, J=5.3, 1H); 8.12-8.11 (m, 1H); 8.10-8.08 (m, 1H); 8.01 (d, J=5.3, 1H); 7.78 (d, J=8.3, 2H); 7.65-7.62 (m, 1H); 7.57 (t, J=7.8, 1H); 7.45 (d, J=8.3, 2H); 2.79 (t, J=7.5, 2H); 2.19 (t, J=7.3, 2H); 1.69-1.63 (m, 2H); 1.56-1.50 (m, 2H) |
| 51 | (structure) | 8.82 (d, J=5.5, 1H); 8.15 (d, J=7.3, 1H); 8.12-8.08 (m, 2H); 8.00 (d, J=5.2, 1H); 7.78 (d, J=8.2, 2H); 7.65-7.62 (m, 1H); 7.57 (t, J=7.8, 1H); 7.46 (d, J=8.2, 2H); 4.16 (quintett, J=7.2, 1H); 3.05-2.95 (m, 2H); 2.58-2.52 (m, 2H); 1.22 (d, J=7.3, 3H) |
| 52 | (structure) | 12.40 (br., 1H); 8.83 (d, J=5.5, 1H); 8.11-8.08 (m, 2H); 8.05 (d, J=7.3, 1H); 8.02 (d, J=5.5, 1H); 7.78 (d, J=8.5, 2H); 7.64-7.62 (m, 1H); 7.57 (t, J=7.8, 1H); 7.47 (d, J=8.2, 2H); 4.16-4.09 (m, 1H); 2.80-2.76 (m, 2H); 2.16 (t, J=7.3, 2H); 1.89-1.81 (m, 2H); 1.17 (d, J=7.3, 3H) |
| 53 | (structure) | 8.78 (d, J=5.2, 1H); 8.09-8.06 (m, 2H); 7.97 (d, J=5.2, 1H); 7.95 (d, J=7.5, 1H); 7.83 (d, J=8.5, 2H); 7.64-7.62 (m, 1H); 7.57 (t, J=7.8, 1H); 7.52 (d, J=8.5, 2H); 4.90 (s, 2H); 4.26-4.18 (m, 1H); 4.01 (s, 2H); 1.24 (d, J=7.0, 3H) |

EXAMPLE 54

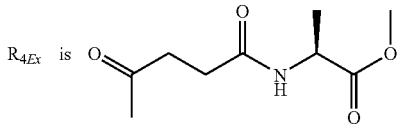

1.97 ml of diisopropylethyl amine are added dropwise to a mixture of 2 g of N-[4-(3-chloro-phenyl)-pyrimidin-2-yl]-N-(4-trifluoromethyl-phenyl)-amine, 1.21 ml of succinyl chloride and 10 mg of dimethylaminopyridine in CH$_2$Cl$_2$. The mixture is stirred at RT, cooled and 2 g of L-alanine methyl ester hydrochloride are added. 3.4 ml of diisopropyl ethylamine are added dropwise to the mixture and stirred further. The mixture obtained is diluted with ethylacetate, washed and dried. Solvent is evaporated and the product is obtained after crystallisation (m.p. 170.9° C.).

(d$_6$-DMSO, 500 MHz, RT): 8.83 (d, J=5.3, 1H); 8.31 (d, J=7.0, 1H); 8.12-8.08 (m, 2H); 8.01 (d, J=5.3, 1H); 7.79 (d, J=8.4, 2H); 7.64-7.62 (m, 1H); 7.57 (t, J=7.9, 1H); 7.46 (d, J=8.2, 2H); 4.24 (quintett, J=7.2, 1H); 3.58 (s, 3H); 3.04-2.98 (m, 2H); 2.60-2.51 (m, 2H); 1.24 (d, J=7.3, 3H)

Analogously as described in example 54 but using appropriate starting material, compounds of formula I, wherein R$_4$ is as described in TABLE 7 below, having $^1$H-NMR (d$_6$-DMSO, 500 MHz, RT) or m.p. as defined in TABLE 7 are obtained:

TABLE 7

| Example | R$_{4EX}$ | m.p./$^1$H-NMR |
|---|---|---|
| 55 | (structure) | 12.61 (br.); 8.82 (d, J=5.3, 1H); 8.09-8.06 (m, 3H); 8.01 (d, J=5.2, 1H); 7.78 (d, J=8.7, 2H); 7.63-7.61 (m, 1H); 7.58-7.54 (m, 1H); 7.45 (d, J=8.3, 2H); 7.21-7.13 (m, 5H); 4.40-4.35 (m, 1H); 3.00 (dd, J=13.9, 4.8, 1H); 2.79 (dd, J=13.8, 9.7, 1H); 2.69 (t, J=7.3, 2H); 2.12-2.08 (m, 2H); 1.79 (quintet, J=7.3, 2H) |
| 56 | (structure) | 8.82 (d, J=5.5, 1H); 8.13-8.12 (m, 1H); 8.11-8.09 (m, 1H); 8.00 (d, J=5.2, 1H); 7.79 (d, J=8.2, 2H); 7.65-7.62 (m, 1H); 7.57 (t, J=7.9, 1H); 7.46 (d, J=8.2, 2H); 3.35-3.21 (m, 4H); 2.99-2.96 (m, 2H); 2.70-2.67 (m, 2H); 1.09 (t, J=7.0, 3H); 0.98 (t, J=7.0, 3H) |

TABLE 7-continued

| Example | R$_{4EX}$ | m.p./$^1$H-NMR |
|---|---|---|
| 57 | 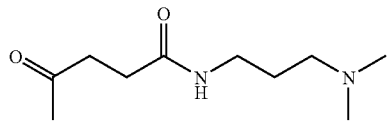 | 8.82 (d, J=5.3, 1H); 8.12-8.07 (m, 2H); 8.00 (d, J=5.3, 1H); 7.83 (t, J=5.6, 1H); 7.78 (d, J=8.8, 2H); 7.63 (m, 1H); 7.56 (t, J=7.8, 1H); 7.45 (d, J=8.6, 2H); 3.04-2.96 (m, 4H); 2.45 (m); 2.17 (t, J=7.2, 2H); 2.07 (s, 6H); 1.47 (quintett, J=7.1, 2H) |
| 58 | 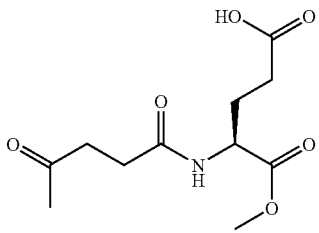 | (400 MHz): 8.82 (d, J=5.3, 1H); 8.31 (d, J=7.7, 1H); 8.11-8.08 (m, 2H); 8.01 (d, J=5.3, 1H); 7.77 (d, J=8.7, 2H); 7.64-7.61 (m, 1H); 7.56 (t, J=7.7, 1H); 7.44 (d, J=8.2, 2H); 4.28-4.23 (m, 1H); 3.58 (s, 3H); 2.97 (m, 2H); 2.62-2.48 (m); 2.25 (t, J=7.5, 2H); 1.90 (m, 1H); 1.75 (m, 1H) |
| 59 | 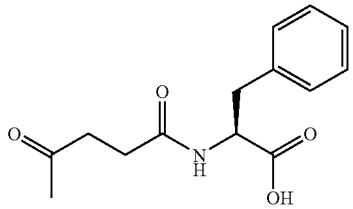 | 12.64 (br); 8.82 (d, J=5.2, 1H); 8.21 (d, J=8.0, 1H); 8.11-8.07 (m, 2H); 8.01 (d, J=5.3, 1H); 7.77 (d, J=8.5, 2H); 7.64-7.61 (m, 1H); 7.56 (t, J=7.9, 1H); 7.45 (d, J=8.3, 2H); 7.22-7.11 (m, 5H); 4.40 (dt, 1H); 3.01 (dd, J=13.8, 5.1, 1H); 2.92-2.88 (m, 2H); 2.83 (dd, J=13.7, 9.1, 1H); 2.55-2.43 (m) |
| 60 | 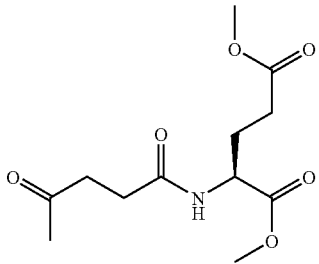 | 8.83 (d, J=5.3, 1H); 8.30 (d, J=7.5, 1H); 8.12-8.08 (m, 2H); 8.01 (d, J=5.3, 1H); 7.78 (d, J=8.9, 2H); 7.64-7.62 (m, 1H); 7.57 (t, J=7.9, 1H); 7.45 (d, J=8.4, 2H); 4.27 (dt, J=5.3, 8.3, 1H); 3.59 (s, 3H); 3.55 (s, 3H); 3.04-2.96 (m, 2H); 2.62-2.49 (m, 2H); 2.38-2.31 (m, 2H); 1.99-1.92 (m, 1H); 1.83-1.76 (m, 1H) |
| 61 | 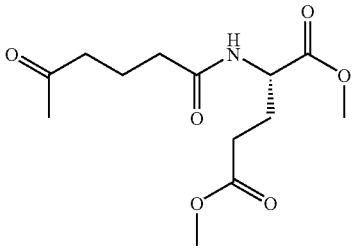 | 8.83 (d, J=5.2, 1H); 8.19 (d, J=7.5, 1H); 8.11-8.07 (m, 2H); 8.02 (d, J=5.3, 1H); 7.78 (d, J=8.6, 2H); 7.64-7.62 (m, 1H); 7.57 (t, J=7.8, 1H); 7.47 (d, J=8.1, 2H); 4.22-4.18 (m, 1H); 3.55 (two singlets, 6H); 2.78 (t, J=7.4, 2H); 2.30 (t, J=7.8, 2H); 2.18 (t, J=7.2, 2H); 1.96-1.84 (m, 3H); 1.80-1.72 (m, 1H) |
| 62 | 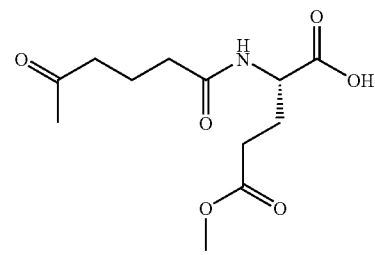 | 8.83 (d, J=5.2, 1H); 8.10-8.07 (m, 2H); 8.05 (d, J=7.6, 1H); 8.01 (d, J=5.2, 1H); 7.78 (d, J=8.9, 2H); 7.63-7.61 (m, 1H); 7.57 (t, J=7.9, 1H); 7.47 (d, J=8.5, 2H); 4.15 (dt, J=5.0, 8.4, 1H); 3.54 (s, 3H); 2.78 (m, 2H); 2.30-2.27 (m, 2H); 2.18 (t, J=7.3, 2H); 1.96-1.90 (m, 1H); 1.88-1.82 (m, 2H); 1.78-1.70 (m, 1H) |

TABLE 7-continued

| Example | R$_{4EX}$ | m.p./$^1$H-NMR |
|---|---|---|
| 63 | | 8.83 (d, J=5.5, 1H); 8.20 (d, J=7.0, 1H); 8.11-8.08 (m, 2H); 8.02 (d, J=5.2, 1H); 7.78 (d, J=8.2, 2H); 7.65-7.62 (m, 1H); 7.57 (t, J=7.9, 1H); 7.47 (d, J=7.9, 2H); 4.21-4.15 (m, 1H); 3.54 (s, 3H); 2.78 (t, J=7.5, 2H); 2.16 (t, J=7.3, 2H); 1.89-1.82 (m, 2H); 1.18 (d, J=7.3, 3H) |
| 64 | | 8.78 (d, J=5.3, 1H); 8.15 (d, J=7.3, 1H); 8.09-8.07 (m, 2H); 7.97 (d, J=5.3, 1H); 7.84 (d, J=8.3, 2H); 7.65-7.62 (m, 1H); 7.58-7.55 (m, 1H); 7.52 (d, J=8.3, 2H); 4.90 (s, 2H); 4.35-4.28 (m, 1H); 4.02 (s, 2H); 3.58 (s, 3H); 1.25 (d, J=7.3, 3H) |
| 65 | | 8.82 (d, 1H); 8.12-8.07 (m, 2H); 8.02 (d, J=7.8, 1H); 8.00 (d, J=5.3, 1H); 7.84 (m, 1H); 7.77 (d, J=8.4, 2H); 7.63-7.61 (m, 1H); 7.55 (t, 1H); 7.45 (d, J=8.2, 2H); 4.12-4.07 (m, 1H); 3.01-2.97 (m, 4H); 2.48-2.45 (m, 2H); 1.80 (s, 3H) |
| 66 | | 8.82 (d, 1H); 8.12-8.07 (m, 2H); 8.00 (d, J=5.3, 1H); 7.78 (d, J=8.3, 2H); 7.63 (m, 1H); 7.56 (t, J=7.9, 1H); 7.45 (d, J=8.1, 2H); 3.25-3.16 (m, 4H); 2.80 (t, J=7.3, 2H); 2.31 (t, J=7.3, 2H); 1.85 (quintett, J=7.3, 2H); 1.00 (t, J=7.1, 3H); 0.92 (t, J=7.1, 3H) |
| 67 | | 8.83 (d, J=5.3, 1H); 8.11-8.07 (m, 2H); 8.01 (d, J=5.3, 1H); 7.80-7.73 (m, 3H); 7.62 (d, 1H); 7.55 (t, 1H); 7.45 (d, J=8.3, 2H); 2.95 (m, 2H); 2.75 (t, J=7.2, 2H); 2.05 (s) |

EXAMPLE 68

R$_{4Ex}$ is 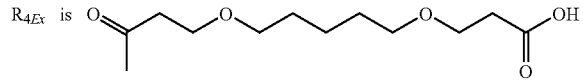

A solution 6.5 g of 3-[5-(2-Chlorocarbonyl-ethoxy)-pentyloxy]-propionyl chloride in 10 ml of CH$_2$Cl$_2$ is added dropwise to a mixture of 1 g of N-[4-3-chloro-phenyl)-pyrimidin-2-yl]-N-(4-trifluoromethyl-phenyl)-amine, 10 mg of dimethylaminopyridine and 2.7 ml of diisopropyl ethylamine in CH$_2$Cl$_2$. The mixture obtained is stirred at RT, cooled and acetonitrile and water are added; the mixture is stirred further. The mixture obtained is extracted with ethylacetate. An organic phase formed is washed, dried, solvent is stripped off and the product is obtained. $^1$H-NMR (d$_6$-DMSO, 500 MHz, RT): 8.83 (d, J=5.2, 1H); 8.12 (t, J=1.9, 1H); 8.10 (dt, J=7.6, 1.5, 1H); 8.02 (d, J=5.4, 1H); 7.79 (d, J=8.3, 2H); 7.64 (m, 1H); 7.57 (t, J=7.9, 1H); 7.44 (d, J=8.1, 2H); 3.68 (t, J=6.4, 2H); 3.51 (t, J=6.4, 2H); 3.03 (t, J=6.5, 2H); 2.39 (t, J=6.3, 2H); 1.47-1.39 (m, 4H); 1.28-1.21 (m, 2H)

The invention claimed is:
1. A compound of formula

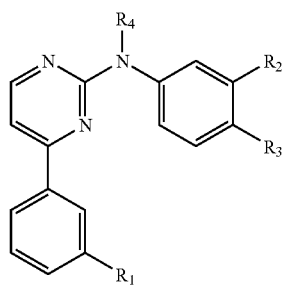

I wherein
R$_1$ is halogen or halo(C$_{1-4}$)alkyl,
R$_2$ is hydrogen, halogen or halo(C$_{1-4}$)alkyl,
R$_3$ is halogen or halo(C$_{1-4}$)alkyl,
R$_4$ is hydrogen, (C$_{1-8}$)alkyl, hydroxy(C$_{1-6}$)alkyl or a group of formula
—CO—R$_5$,
—CO—(CH$_2$)$_m$—OR$_6$, —CO—CO—$R_7$,
—CO—CO—$OR_8$,
—CO—N($R_9R_{10}$),
—CO—$(CH_2)_n$—CO—$R_{11}$,
—CO—$(CHR_{15})$—O—$(CH_2)_o$—CO—$R_{11}$,
—CO—$(CH_2)_p$—O—$(CH_2)_q$—O—$(CH_2)_r$—$R_{16}$,
—CO—O—$(CH_2)_s$—O—CO—$R_{17}$,
—CO—O—$(CH_2)_t$—N($R_{18}R_{19}$),
—CO—O—$(CH_2)_u$—NH—CO—CH($NH_2$)—$R_{20}$, or
—CO—O—$(CH_2)_w$—NH—CO—$R_{17}$, wherein $R_5$ is hydrogen, $(C_{1-8})$alkyl, $(C_{3-8})$cycloalkyl, amino, $(C_{1-4})$alkylamino, di$(C_{1-4})$alkylamino, aryl or heterocyclyl which is a 5 or 6-membered heterocyclic ring system having 1 to 4 heteroatoms selected from N, O or S, $R_6$ is hydrogen, $(C_{1-4})$alkyl, $(C_{3-8})$cycloalkyl, aryl, $(C_{1-4})$alkyl substituted by heterocyclyl which is a 5 or 6-membered heterocyclic ring system having 1 to 4 heteroatoms selected from N, O or S, amino$(C_{1-6})$alkyl, $(C_{1-4})$alkylamino$(C_{1-6})$alkyl, di$(C_{1-4})$alkylamino$(C_{1-6})$alkyl, hydroxy$(C_{1-6})$alkyl, hydroxy$(C_{1-4})$alkylamino$(C_{1-6})$alkyl or an amino acid residue, $R_7$ and $R_8$ independently of each other are $(C_{1-4})$alkyl, $(C_{3-8})$cycloalkyl, aryl or heterocyclyl which is a 5 or 6-membered heterocyclic ring system having 1 to 4 heteroatoms selected from N, O or S, $R_9$ and $R_{10}$ independently of each other are hydrogen or $(C_{1-4})$alkyl or one of $R_9$ and $R_{10}$ is hydrogen and the other is $(C_{3-8})$cycloalkyl, $(C_{1-4})$alkyl, aryl or heterocyclyl, $R_{11}$ is $(C_{1-4})$alkyl, —$OR_{12}$, —$NR_{13}R_{14}$, an amino acid, an $(C_{1-4})$alkylester thereof or a di$(C_{1-4})$alkylester thereof, $R_{12}$ is hydrogen or $(C_{1-4})$alkyl, $R_{13}$ and $R_{14}$ independently of each other are hydrogen, $(C_{1-4})$alkyl, amino$(C_{1-6})$alkyl, $(C_{1-4})$alkylamino$(C_{1-6})$alkyl, di$(C_{1-4})$alkylamino$(C_{1-6})$alkyl, $R_{15}$ is hydrogen or $(C_{1-4})$alkyl, $R_{16}$ is hydrogen, $(C_{1-4})$alkyl, carboxyl or carboxylic ester, $R_{17}$ is amino$(C_{1-4})$alkyl, $(C_{1-4})$alkylamino$(C_{1-4})$alkyl or di$(C_{1-4})$alkylamino$(C_{1-4})$alkyl, $R_{18}$ is hydrogen or $(C_{1-4})$alkyl, $R_{19}$ is hydroxy$(C_{1-4})$alkyl, $R_{20}$ is $(C_{1-4})$alkyl or hydroxy$(C_{1-4})$alkyl, m is 0 to 4,
n is 2 to 8,
o is 0 to 4,
p is 0 to 4,
q is 1 to 8,
r is 0 to 4,
s is 1 to 4,
t is 1 to 4,
u is 1 to 6 and
w is 1 to 6, or a salt thereof.

2. A compound of claim 1 wherein $R_1$ is chloro or trifluoromethyl,
$R_2$ is hydrogen or trifluoromethyl,
$R_3$ is chloro, fluoro or trifluoromethyl,
$R_4$ is hydrogen, $(C_{1-4})$alkyl, e.g. methyl, hydroxy$(C_{1-4})$alkyl, e.g. hydroxyethyl, or a group of formula
—CO—$R_5$,
—CO—$(CH_2)_m$—$OR_6$,
—CO—CO—$R_7$,
—CO—CO—$OR_8$,
—CO—N($R_9R_{10}$),
—CO—$(CH_2)_n$—CO—$R_{11}$,
—CO—$(CHR_{15})$—O—$(CH_2)_o$—CO—$R_{11}$,
—CO—$(CH_2)_p$—O—$(CH_2)_q$—O—$(CH_2)_r$—$R_{16}$,
—CO—O—$(CH_2)_s$—O—CO—$R_{17}$,
—CO—O—$(CH_2)_t$—N($R_{18}R_{19}$),
—CO—O—$(CH_2)_u$—NH—CO—CH($NH_2$)—$R_{20}$, or
—CO—O—$(CH_2)_w$—NH—CO—$R_{17}$, wherein $R_5$ is hydrogen, $(C_{1-4})$alkyl, $(C_{3-6})$cycloalkyl, dimethylamino, phenyl or heterocyclyl which is a 6-membered heterocyclic ring system having one O as a heteroatom, e.g. tetrahydropyranyl, $R_6$ is hydrogen, $(C_{1-4})$alkyl, $(C_{1-2})$alkyl substituted by heterocyclyl which is a 5 or 6-membered heterocyclic ring system having 1 or 2 heteroatoms selected from N or O, e.g. including unsubstituted pyrrolidine, morpholine and piperazine and piperazine substituted by e.g. $(C_{1-2})$alkyl or $(C_{1-2})$hydroxyalkyl; amino$(C_{1-4})$alkyl, $(C_{1-2})$alkylamino$(C_{1-4})$alkyl, di$(C_{1-2})$alkylamino$(C_{1-4})$alkyl, hydroxy$(C_{1-3})$alkyl, hydroxy$(C_{1-2})$alkylamino$(C_{1-2})$alkyl or an amino acid residue, $R_7$ and $R_8$ independently of each other are $(C_{1-2})$alkyl or phenyl, $R_9$ and $R_{10}$ independently of each other are hydrogen or $(C_{1-2})$alkyl, $R_{11}$ is $(C_{1-2})$alkyl, —$OR_{12}$, —$NR_{13}R_{14}$, an amino acid, an $(C_{1-2})$alkylester thereof or an di$(C_{1-2})$alkylester thereof, $R_{12}$ is hydrogen or $(C_{1-2})$alkyl, $R_{13}$ and $R_{14}$ independently of each other are hydrogen, $(C_{1-2})$alkyl, amino$(C_{1-4})$alkyl, $(C_{1-2})$alkylamino$(C_{1-4})$alkyl, di$(C_{1-2})$alkylamino$(C_{1-4})$alkyl, $R_{15}$ is hydrogen or $(C_{1-2})$alkyl, $R_{16}$ is hydrogen, $(C_{1-2})$alkyl, carboxyl or carboxylic ester, $R_{17}$ is amino$(C_{1-2})$alkyl, $R_{18}$ is hydrogen or $(C_{1-2})$alkyl, $R_{19}$ is hydroxy$(C_{1-2})$alkyl, $R_{20}$ is $(C_{1-2})$alkyl or hydroxy$(C_{1-2})$alkyl, m is 0 or 1,
n is 2 to 4,
o is 0 or 1,
p is 0 to 2,
q is 2 to 5,
r is 0 to 2,
s is 2,
t is 2,
u is 1 to 3 and
w is 1 to 3.

3. A compound according to claim 1 which is a compound of formula I wherein $R_1$ is chloro,
$R_2$ is hydrogen,
$R_3$ is trifluoromethyl and
$R_4$ is hydrogen.

4. A compound according to claim 1 which is a compound of formula I wherein $R_1$ is chloro,
$R_2$ is hydrogen,
$R_3$ is trifluoromethyl and
$R_4$ is a group of formula —C—O—$(CH_2)_2$—N[($C_2H_5$OH)($CH_3$)].

5. A compound according to claim 1 in the form of a salt.

6. A method of treatment of rheumatoid arthritis which method comprises administering a therapeutically effective amount of a compound of claim 1 to a subject in need of such treatment.

7. A pharmaceutical composition comprising a compound of claim 1 association with at least one pharmaceutical excipient.

* * * * *